US009675804B2

(12) United States Patent
Whiting et al.

(10) Patent No.: US 9,675,804 B2
(45) Date of Patent: *Jun. 13, 2017

(54) MEDICAL MONITORING AND TREATMENT DEVICE WITH EXTERNAL PACING

(71) Applicant: ZOLL MEDICAL CORPORATION, Chelmsford, MA (US)

(72) Inventors: Jason T. Whiting, Gibsonia, PA (US); Thomas E. Kaib, Irwin, PA (US); Rachel H. Carlson, Falls Creek, PA (US); Gregory R. Frank, Mt. Lebanon, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/079,294

(22) Filed: Mar. 24, 2016

(65) Prior Publication Data

US 2016/0206886 A1 Jul. 21, 2016

Related U.S. Application Data

(63) Continuation of application No. 14/610,600, filed on Jan. 30, 2015, now Pat. No. 9,320,904, which is a (Continued)

(51) Int. Cl.
*A61N 1/00* (2006.01)
*A61N 1/365* (2006.01)
(Continued)

(52) U.S. Cl.
CPC .......... *A61N 1/36592* (2013.01); *A61B 5/046* (2013.01); *A61B 5/04085* (2013.01);
(Continued)

(58) Field of Classification Search
CPC .................................. A61N 1/362; A61N 1/39
See application file for complete search history.

(56) References Cited

U.S. PATENT DOCUMENTS

| 4,094,310 A | 6/1978 | McEachern et al. |
| 4,393,874 A | 7/1983 | Nappholz et al. |

(Continued)

FOREIGN PATENT DOCUMENTS

| CN | 1658927 A | 8/2005 |
| CN | 102458572 A | 5/2012 |

(Continued)

OTHER PUBLICATIONS

American Journal of Respiratory and Critical Care Medicine, vol. 166, pp. 111-117 (2002). American Thoracic Society, ATS Statement Guidelines for the Six-Minute Walk Test, available at http://ajrccm.atsjournals.org/cgi/content/full/166/1/111.

(Continued)

*Primary Examiner* — Robert N Wieland
(74) *Attorney, Agent, or Firm* — Lando & Anastasi, LLP

(57) ABSTRACT

A non-invasive bodily-attached ambulatory medical monitoring and treatment device with pacing is provided. The device includes at least one therapy electrode; a memory storing information indicative of a patient's cardiac activity; circuitry for implementing a plurality of pacing routines, each pacing routine of the plurality of pacing routines corresponding to at least one cardiac condition of a plurality of cardiac conditions; and at least one processor coupled to the circuitry and configured to identify, within the information, at least one cardiac condition of the plurality of cardiac conditions; and respond to the identified cardiac condition in part by causing execution of at least one pacing routine corresponding to the identified cardiac condition.

28 Claims, 4 Drawing Sheets

Related U.S. Application Data continuation of application No. 13/907,523, filed on May 31, 2013, now Pat. No. 8,983,597.

(60) Provisional application No. 61/653,889, filed on May 31, 2012.

(51) Int. Cl.
*A61N 1/362* (2006.01)
*A61N 1/39* (2006.01)
*A61B 5/00* (2006.01)
*A61B 5/0408* (2006.01)
*A61B 5/046* (2006.01)
*A61N 1/04* (2006.01)
*A61N 1/37* (2006.01)

(52) U.S. Cl.
CPC ............ *A61B 5/6831* (2013.01); *A61N 1/046* (2013.01); *A61N 1/0484* (2013.01); *A61N 1/362* (2013.01); *A61N 1/3621* (2013.01); *A61N 1/3625* (2013.01); *A61N 1/371* (2013.01); *A61N 1/3925* (2013.01); *A61N 1/3987* (2013.01)

(56) References Cited

U.S. PATENT DOCUMENTS

| | | | |
|---|---|---|---|
| 4,632,122 A | 12/1986 | Johansson et al. |
| 4,928,690 A | 5/1990 | Heilman et al. |
| 4,978,926 A | 12/1990 | Zerod et al. |
| 5,062,834 A | 11/1991 | Gross et al. |
| 5,078,134 A | 1/1992 | Heilman et al. |
| 5,205,284 A | 4/1993 | Freeman |
| 5,282,843 A | 2/1994 | Freeman |
| 5,330,505 A | 7/1994 | Cohen |
| 5,348,008 A | 9/1994 | Bornn et al. |
| 5,357,696 A | 10/1994 | Gray et al. |
| 5,365,932 A | 11/1994 | Greenhut |
| 5,431,688 A | 7/1995 | Freeman |
| 5,662,689 A | 9/1997 | Elsberry et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,797,967 A | 8/1998 | KenKnight |
| 5,929,601 A | 7/1999 | Kaib et al. |
| 5,944,669 A | 8/1999 | Kaib |
| 6,016,445 A | 1/2000 | Baura |
| 6,045,503 A | 4/2000 | Grabner et al. |
| 6,058,328 A | 5/2000 | Levine et al. |
| 6,065,154 A | 5/2000 | Hulings et al. |
| 6,097,987 A | 8/2000 | Milani |
| 6,148,233 A | 11/2000 | Owen et al. |
| 6,169,387 B1 | 1/2001 | Kaib |
| 6,169,397 B1 | 1/2001 | Steinbach et al. |
| 6,253,099 B1 | 6/2001 | Oskin et al. |
| 6,280,461 B1 | 8/2001 | Glegyak et al. |
| 6,390,996 B1 | 5/2002 | Halperin et al. |
| 6,406,426 B1 | 6/2002 | Reuss et al. |
| 6,681,003 B2 | 1/2004 | Linder et al. |
| 6,690,969 B2 | 2/2004 | Bystrom et al. |
| 6,804,554 B2 | 10/2004 | Ujhelyi et al. |
| 6,827,695 B2 | 12/2004 | Palazzolo et al. |
| 6,865,413 B2 | 3/2005 | Halperin et al. |
| 6,889,078 B2 | 5/2005 | Struble et al. |
| 6,889,079 B2 | 5/2005 | Bocek et al. |
| 6,908,437 B2 | 6/2005 | Bardy |
| 6,990,373 B2 | 1/2006 | Jayne et al. |
| 7,074,199 B2 | 7/2006 | Halperin et al. |
| 7,108,665 B2 | 9/2006 | Halperin et al. |
| 7,118,542 B2 | 10/2006 | Palazzolo et al. |
| 7,122,014 B2 | 10/2006 | Palazzolo et al. |
| 7,130,690 B2 | 10/2006 | Rueter et al. |
| 7,149,579 B1 | 12/2006 | Koh et al. |
| 7,220,235 B2 | 5/2007 | Geheb et al. |
| 7,295,871 B2 | 11/2007 | Halperin et al. |
| 7,340,296 B2 | 3/2008 | Stahmann et al. |
| 7,427,921 B2 | 9/2008 | Van Woudenberg |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,831,303 B2 | 11/2010 | Rueter et al. |
| 7,974,689 B2 | 7/2011 | Volpe et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 2003/0004547 A1 | 1/2003 | Owen et al. |
| 2003/0095648 A1 | 5/2003 | Kaib et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0191404 A1 | 10/2003 | Klein |
| 2003/0195567 A1 | 10/2003 | Jayne et al. |
| 2003/0212311 A1 | 11/2003 | Nova et al. |
| 2004/0007970 A1 | 1/2004 | Ma et al. |
| 2004/0049233 A1 | 3/2004 | Edwards |
| 2005/0049515 A1 | 3/2005 | Misczynski et al. |
| 2005/0131465 A1 | 6/2005 | Freeman et al. |
| 2006/0036292 A1 | 2/2006 | Smith et al. |
| 2006/0085049 A1 | 4/2006 | Cory et al. |
| 2006/0178706 A1 | 8/2006 | Lisogurski et al. |
| 2006/0220809 A1 | 10/2006 | Stigall et al. |
| 2006/0264776 A1 | 11/2006 | Stahmann et al. |
| 2006/0270952 A1 | 11/2006 | Freeman et al. |
| 2007/0073120 A1 | 3/2007 | Li et al. |
| 2007/0118056 A1 | 5/2007 | Wang et al. |
| 2007/0161913 A1 | 7/2007 | Farrell et al. |
| 2007/0169364 A1 | 7/2007 | Townsend et al. |
| 2007/0239220 A1 | 10/2007 | Greenhut et al. |
| 2007/0265671 A1 | 11/2007 | Roberts et al. |
| 2008/0004536 A1 | 1/2008 | Baxi et al. |
| 2008/0030656 A1 | 2/2008 | Watson et al. |
| 2008/0031270 A1 | 2/2008 | Tran et al. |
| 2008/0033495 A1 | 2/2008 | Kumar |
| 2008/0045815 A1 | 2/2008 | Derchak et al. |
| 2008/0058884 A1 | 3/2008 | Matos |
| 2008/0221397 A1* | 9/2008 | McMahon ............... A61N 1/39 600/301 |
| 2008/0249591 A1 | 10/2008 | Gaw et al. |
| 2008/0306562 A1 | 12/2008 | Donnelly et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0093687 A1 | 4/2009 | Telfort et al. |
| 2009/0138059 A1 | 5/2009 | Ouwerkerk |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0234716 A1 | 9/2010 | Engel |
| 2010/0268291 A1 | 10/2010 | Imran |
| 2010/0295674 A1 | 11/2010 | Hsieh et al. |
| 2010/0298899 A1 | 11/2010 | Donnelly et al. |

(56) References Cited

U.S. PATENT DOCUMENTS

| | | |
|---|---|---|
| 2010/0312297 A1 | 12/2010 | Volpe et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150244 A1 | 6/2012 | Freeman et al. |
| 2012/0158075 A1 | 6/2012 | Kaib et al. |
| 2013/0338724 A1 | 12/2013 | Joo et al. |
| 2014/0364918 A1 | 12/2014 | Owen et al. |

FOREIGN PATENT DOCUMENTS

| | | | |
|---|---|---|---|
| EP | 0295497 | B1 | 9/1993 |
| EP | 0335356 | B1 | 3/1996 |
| EP | 1455640 | B1 | 1/2008 |
| EP | 1720446 | B1 | 7/2010 |
| JP | 5115450 | A | 5/1993 |
| JP | H10-127781 | A | 5/1998 |
| JP | 2002200059 | A | 7/2002 |
| WO | 0002484 | A1 | 1/2000 |
| WO | 2004054656 | A1 | 7/2004 |
| WO | 2006050325 | A2 | 5/2006 |
| WO | 2007057169 | A1 | 5/2007 |
| WO | 2007077997 | A1 | 7/2007 |
| WO | 2010025432 | A1 | 3/2010 |

OTHER PUBLICATIONS

DeBock et al., "Captopril treatment of chronic heart failure in the very old," J. Gerontol. (1994) 49: M148-M152.

Internation Search Report and Written Opinion from corresponding PCT application PCT/US2013/043736, dated Sep. 4, 2013.

O'Keeffe et al., "Reproducability and responsiveness of quality of the assessment and six minute walk test in elderly heart failure patients," Heart (1998) 80: 377-382.

Reek et al. Clinical Efficacy of a Wearable Defibrillator Acutely Terminating Episodes of Ventricular Fibrillation Using Biphasic Shock.

\* cited by examiner

MEDICAL MONITORING AND TREATMENT DEVICE WITH EXTERNAL PACING

RELATED APPLICATIONS

This application claims the benefit under 35 U.S.C. §120 as a continuation of U.S. application Ser. No. 14/610,600 titled "MEDICAL MONITORING AND TREATMENT DEVICE WITH EXTERNAL PACING" filed on Jan. 30, 2015, now U.S. Pat. No. 9,320,904, which is a continuation of U.S. application Ser. No. 13/907,523 titled "MEDICAL MONITORING AND TREATMENT DEVICE WITH EXTERNAL PACING" filed on May 31, 2013, now U.S. Pat. No. 8,983,597, which claims priority under 35 U.S.C. §119(e) to U.S. Provisional Application Ser. No. 61/653,889, titled "NONINVASIVE AMBULATORY MONITORING AND TREATMENT DEVICE WITH EXTERNAL PACING," filed on May 31, 2012, each of which is hereby incorporated herein by reference in its entirety.

BACKGROUND OF THE INVENTION

1. Technical Field

The present invention is directed to noninvasive ambulatory medical devices, and more particularly, to a noninvasive medical monitoring and treatment device that is capable of externally pacing the heart of a patient wearing the device.

2. Discussion of the Related Art

Cardiac arrest and other cardiac health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival.

To protect against cardiac arrest and other cardiac health ailments, some at-risk patients may use a wearable defibrillator, such as the LifeVest® wearable cardioverter defibrillator available from ZOLL Medical Corporation of Chelmsford, Mass. To remain protected, the patient wears the device nearly continuously while going about their normal daily activities, while awake, and while asleep.

SUMMARY OF THE INVENTION

Some aspects and embodiments of the present invention administer external pacing to the heart using a non-invasive bodily-attached ambulatory medical monitoring and treatment device (hereinafter referred to as a "medical monitoring and treatment device"). As used herein, the term non-invasive means that the device does not penetrate the body of a patient. This is in contrast to invasive devices, such as implantable medical devices, in which at least a portion of the device is disposed subcutaneously. The term bodily-attached means that at least a portion of the device (other than its electrodes in the case of a defibrillator, cardioverter or pacer) is removably attached to the body of a patient, such as by mechanical coupling (for example, by a wrist strap, cervical collar, bicep ring), adhesion (for example, by an adhesive gel intermediary), suction, magnetism, fabric or other flexible material (for example, by straps or integration into a garment) or other body mounting features not limited by the aforementioned examples. These coupling elements hold the device in a substantially fixed position with respect to the body of the patient. The term ambulatory means that the device is capable of and designed for moving with the patient as the patient goes about their daily routine.

One example of a medical monitoring and treatment device is the LifeVest® Wearable Cardioverter Defibrillator available from ZOLL Medical Corporation of Chelmsford, Mass. A medical monitoring and treatment device can provide life saving defibrillation treatment to a patient suffering a treatable form of cardiac arrhythmia such as Ventricular Fibrillation (VF) or Ventricular Tachycardia (VT). Applicants have appreciated that such a medical monitoring and treatment device can be configured to perform a variety of different types of cardiac pacing to treat a wide variety of different cardiac arrhythmias, such as bradycardia, tachycardia, an irregular cardiac rhythm, and asystole (including asystole after a shock). Applicants have further appreciated that, in other embodiments, a medical monitoring and treatment device can be configured to perform pacing to treat pulseless electrical activity. In accordance with an aspect of the present invention, the medical monitoring and treatment device can be configured to pace the heart of the patient at a fixed energy level (e.g., fixed current, fixed voltage, etc. . . . ) and pulse rate, to pace the heart of the patient on demand with a fixed energy level and an adjustable rate responsive to the detected intrinsic activity level of the patient's heart, or to pace the heart of the patient using capture management with an adjustable energy level and adjustable rate responsive to the detected intrinsic rate of the patient's heart and the detected response of the patient's heart to pacing, including both on a beat-by-beat basis and as analyzed over other various time intervals.

According to some embodiments, a medical monitoring and treatment device is provided. The medical monitoring and treatment device includes a battery, at least one therapy electrode coupled to the battery, a memory storing information indicative of a patient's cardiac activity, and at least one processor coupled to the memory and the at least one therapy electrode. The at least one processor is configured to identify a cardiac arrhythmia within the information and execute at least one pacing routine to treat the identified cardiac arrhythmia.

In the medical monitoring and treatment device, the cardiac arrhythmia that the at least one processor is configured to identify may include bradycardia and the at least one pacing routine may be configured to determine that a first interval has passed without detection of a heart beat and apply, responsive to determining that the first interval has passed, a pacing pulse via the at least one therapy electrode. The first interval may be defined by a base pacing rate and a hysteresis rate. The at least one pacing routine may be further configured to detect an intrinsic heart beat prior to passage of a second interval; determine a third interval based on the base pacing rate, the hysteresis rate, and a point where the intrinsic heart beat was detected; and determine whether another intrinsic heart beat occurs within the third interval.

In the medical monitoring and treatment device, the cardiac arrhythmia that the at least one processor is configured to identify may include tachycardia and the at least one pacing routine may be configured to detect a plurality of intrinsic heart beats prior to passage of a first interval, the plurality of intrinsic heart beats having an intrinsic frequency, the first interval being defined by an anti-tachyarrhythmic pacing rate and apply, responsive to detecting the intrinsic frequency, a series of pacing pulses via the at least one therapy electrode, the series of pacing pulses having a frequency above the intrinsic frequency. The at least one pacing routine may be further configured to detect, after applying the series of pacing pulses, whether another plurality of intrinsic heart beats occur within a second interval, the second interval being defined by the anti-tachyarrhythmic pacing rate.

In the medical monitoring and treatment device, the cardiac arrhythmia that the at least one processor is configured to identify may include an erratic heart rate and the at least one pacing routine may be configured to identify a first series of heart beats within the information, the first series having a lower frequency; identify a second series of heart beats within the information, the second series a upper frequency; and apply, responsive to identifying the erratic heart rate, a series of pacing pulses via the at least one therapy electrode, the series of pacing pulses having a frequency above the lower frequency and below the upper frequency.

In the medical monitoring and treatment device, the cardiac arrhythmia that the at least one processor is configured to identify may include at least one of asystole and pulseless electrical activity and the at least one pacing routine may be configured to determine that a first interval has passed without detection of a heart beat; and apply, responsive to determining that the first interval has passed, a pacing pulse via the at least one therapy electrode. The at least on pacing routine may be further configured to apply a defibrillating shock prior to applying the pacing pulse.

In the medical monitoring and treatment device, the at least one pacing routine may be further configured to determine whether the at least one pacing routine resulted in capture and adjust, responsive to determining that capture did not result, the characteristics of pacing pulses applied during subsequent executions of the at least one pacing routine. The characteristics of the pacing pulses subject to adjustment may include a pulse energy level, a pulse rate, and a pulse width.

In the medical monitoring and treatment device, the at least one pacing routine is further configured to determine whether the at least one pacing routine resulted in capture; and adjust, responsive to determining that capture did result, the characteristics of pacing pulses applied during subsequent executions of the at least one pacing routine.

According to other embodiments, a non-invasive bodily-attached ambulatory wearable defibrillator is provided. The non-invasive bodily-attached ambulatory wearable defibrillator includes a battery, at least one therapy electrode coupled to the battery, a memory storing information indicative of a patient's cardiac activity, and at least one processor coupled to the memory and the at least one therapy electrode. The at least one processor is configured to identify a cardiac arrhythmia within the information and execute at least one pacing routine to treat the identified cardiac arrhythmia.

In the non-invasive bodily-attached ambulatory defibrillator, the cardiac arrhythmia that the at least one processor is configured to identify may include bradycardia and the at least one pacing routine may be configured to determine that a first interval has passed without detection of a heart beat and apply, responsive to determining that the first interval has passed, a pacing pulse via the at least one therapy electrode. The first interval may be defined by a base pacing rate and a hysteresis rate. The at least one pacing routine may be further configured to detect an intrinsic heart beat prior to passage of a second interval; determine a third interval based on the base pacing rate, the hysteresis rate, and a point where the intrinsic heart beat was detected; and determine whether another intrinsic heart beat occurs within the third interval.

In the non-invasive bodily-attached ambulatory defibrillator, the cardiac arrhythmia that the at least one processor is configured to identify may include tachycardia and the at least one pacing routine may be configured to detect a plurality of intrinsic heart beats prior to passage of a first interval, the plurality of intrinsic heart beats having an intrinsic frequency, the first interval being defined by an anti-tachyarrhythmic pacing rate; and apply, responsive to detecting the intrinsic frequency, a series of pacing pulses via the at least one therapy electrode, the series of pacing pulses having a frequency above the intrinsic frequency. The at least one pacing routine may be further configured to detect, after applying the series of pacing pulses, whether another plurality of intrinsic heart beats occur within a second interval, the second interval being defined by the anti-tachyarrhythmic pacing rate.

In the non-invasive bodily-attached ambulatory defibrillator, the cardiac arrhythmia that the at least one processor is configured to identify may include an erratic heart rate and the at least one pacing routine may be configured to identify a first series of heart beats within the information, the first series having a lower frequency; identify a second series of heart beats within the information, the second series a upper frequency; and apply, responsive to identifying the erratic heart rate, a series of pacing pulses via the at least one therapy electrode, the series of pacing pulses having a frequency above the lower frequency and below the upper frequency.

In the non-invasive bodily-attached ambulatory defibrillator, the cardiac arrhythmia that the at least one processor is configured to identify may include at least one of asystole and pulseless electrical activity and the at least one pacing routine may be configured to determine that a first interval has passed without detection of a heart beat and apply, responsive to determining that the first interval has passed, a pacing pulse via the at least one therapy electrode. The at least one pacing routine may be further configured to apply a defibrillating shock prior to applying the pacing pulse.

In the non-invasive bodily-attached ambulatory defibrillator, the at least one pacing routine may be further configured to determine whether the at least one pacing routine resulted in capture and adjust, responsive to determining that capture did not result, the characteristics of pacing pulses applied during subsequent executions of the at least one pacing routine. The characteristics of the pacing pulses subject to adjustment may include a pulse energy level, a pulse rate, and a pulse width.

In the non-invasive bodily-attached ambulatory defibrillator, the at least one pacing routine may be further configured to determine whether the at least one pacing routine resulted in capture and adjust, responsive to determining that capture did result, the characteristics of pacing pulses applied during subsequent executions of the at least one pacing routine.

According to another embodiment, a method of treating cardiac dysfunction using a medical monitoring and treatment device with pacing is provided. The medical monitoring and treatment device may include a non-invasive bodily-attached ambulatory defibrillator. The method includes acts of identifying, by the medical monitoring and treatment device, a cardiac arrhythmia within information indicative of a patient's cardiac activity; and executing, by the medical monitoring and treatment device, at least one pacing routine to treat the identified cardiac arrhythmia.

In the method, where the cardiac arrhythmia includes bradycardia, the act of executing the at least one pacing routine may include acts of determining that a first interval has passed without detection of a heart beat and applying, responsive to determining that the first interval has passed, a pacing pulse via the at least one therapy electrode. The act of determining that the first interval has passed may include an act of defining the first interval using a base pacing rate and a hysteresis rate. The act of executing the at least one pacing routine may include acts of detecting an intrinsic heart beat prior to passage of a second interval; determining a third interval based on the base pacing rate, the hysteresis rate, and a point where the intrinsic heart beat was detected; and determining whether another intrinsic heart beat occurs within the third interval.

In the method, where the cardiac arrhythmia includes tachycardia, the act of executing the at least one pacing routine may include acts of detecting a plurality of intrinsic heart beats prior to passage of a first interval, the plurality of intrinsic heart beats having an intrinsic frequency, the first interval being defined by an anti-tachyarrhythmic pacing rate and applying, responsive to detecting the intrinsic frequency, a series of pacing pulses via the at least one therapy electrode, the series of pacing pulses having a frequency above the intrinsic frequency.

In the method, where the cardiac arrhythmia includes an erratic heart rate, the act of executing the at least one pacing routine may include acts of identifying a first series of heart beats within the information, the first series having a lower frequency; identifying a second series of heart beats within the information, the second series a upper frequency; and applying, responsive to identifying the erratic heart rate, a series of pacing pulses via the at least one therapy electrode, the series of pacing pulses having a frequency above the lower frequency and below the upper frequency.

In the method, where the cardiac arrhythmia includes at least one of asystole and pulseless electrical activity, the act of executing the at least one pacing routine may include acts of determining that a first interval has passed without detection of a heart beat; and applying, responsive to determining that the first interval has passed, a pacing pulse via the at least one therapy electrode. The act of executing the at least one pacing routine may include an act of applying a defibrillating shock prior to applying the pacing pulse.

In the method, the act of executing the at least one pacing routine may include acts of determining whether the at least one pacing routine resulted in successful capture and adjusting, responsive to determining that capture did not result, the characteristics of pacing pulses applied during subsequent executions of the at least one pacing routine. The act of adjusting the characteristics may include an act of adjusting at least one of a pulse energy level, a pulse rate, and a pulse width.

According to one aspect of the present invention, a non-invasive ambulatory medical monitoring and treatment device is provided comprising at least one therapy electrode, a memory storing information indicative of a patient's cardiac activity, circuitry for implementing a plurality of pacing routines, each pacing routine of the plurality of pacing routines corresponding to at least one cardiac condition of a plurality of cardiac conditions, and at least one processor coupled to the circuitry and configured to identify, within the information, at least one cardiac condition of the plurality of cardiac conditions, and respond to the identified cardiac condition in part by causing execution of at least one pacing routine corresponding to the identified cardiac condition. According to one embodiment, the identified cardiac condition includes bradycardia and the at least one pacing routine is configured to determine that a first interval has passed without detection of a heart beat, and apply, responsive to determining that the first interval has passed, a pacing pulse via the at least one therapy electrode. According to one embodiment, the first interval is defined by a base pacing rate and a hysteresis rate. According to another embodiment, the at least one pacing routine is further configured to detect an intrinsic heart beat prior to passage of a second interval, determine a third interval based on the base pacing rate, the hysteresis rate, and a point where the intrinsic heart beat was detected, and determine whether another intrinsic heart beat occurs within the third interval.

According to an alternative embodiment, the identified cardiac condition includes tachycardia and the at least one pacing routine is configured to detect a plurality of intrinsic heart beats prior to passage of a first interval, the plurality of intrinsic heart beats having an intrinsic frequency, the first interval being defined by an anti-tachyarrhythmic pacing rate, and apply, responsive to detecting the intrinsic frequency, a series of pacing pulses via the at least one therapy electrode, the series of pacing pulses having a frequency above the intrinsic frequency. According to one embodiment, the identified cardiac condition includes an erratic heart rate and the at least one pacing routine is configured to identify a first series of heart beats within the information, the first series having a lower frequency, identify a second series of heart beats within the information, the second series having an upper frequency, and apply, responsive to identifying the erratic heart rate, a series of pacing pulses via the at least one therapy electrode, the series of pacing pulses having a frequency above the lower frequency and below the upper frequency. According to another embodiment, the identified cardiac condition includes at least one of asystole and pulseless electrical activity and the at least one pacing routine is configured to determine that a first interval has passed without detection of a heart beat, and apply, responsive to determining that the first interval has passed, a pacing pulse via the at least one therapy electrode. According to an alternative embodiment, the at least one pacing routine is further configured to apply a defibrillating shock prior to applying the pacing pulse.

According to yet another embodiment of the non-invasive ambulatory medical monitoring and treatment device, the at least one pacing routine is further configured to determine whether the at least one pacing routine resulted in capture, and adjust, responsive to determining that capture did not result, the characteristics of pacing pulses applied during subsequent executions of the at least one pacing routine. According to one embodiment, the at least one pacing routine is further configured to determine whether the at least one pacing routine resulted in capture, and adjust, responsive to determining that capture did result, the characteristics of pacing pulses applied during subsequent executions of the at least one pacing routine. According to one embodiment, the characteristics of the pacing pulses subject to adjustment include a pulse energy level, a pulse rate, and a pulse width. According to another embodiment, a method of treating cardiac dysfunction using a non-invasive ambulatory medical monitoring and treatment device is provided having at least one treatment electrode and implementing a plurality of pacing routines, the method comprising identifying, within information indicative of a patient's cardiac activity by the non-invasive ambulatory medical monitoring and treatment device, a cardiac condition from the plurality of cardiac conditions, and responding to the identified cardiac condition at least in part by executing, by the non-invasive ambulatory medical monitoring and treatment device, at least one pacing routine of the plurality of pacing routines, the at least one pacing routine associated with the identified cardiac condition.

According to one embodiment, the identified cardiac condition includes bradycardia, further comprising determining, by the non-invasive ambulatory medical monitoring and treatment device, that a first interval has passed without detection of a heart beat, and applying, responsive to determining that the first interval has passed, a pacing pulse via the at least one therapy electrode. According to one embodiment, the first interval is defined by a base pacing rate and a hysteresis rate. According to another embodiment, the method further comprises detecting, by the non-invasive ambulatory medical monitoring and treatment device, an intrinsic heart beat prior to passage of a second interval, determining a third interval based on the base pacing rate, the hysteresis rate, and a point where the intrinsic heart beat was detected, and determining whether another intrinsic heart beat occurs within the third interval. According to an alternative embodiment, the identified cardiac condition includes tachycardia, further comprises detecting, by the non-invasive ambulatory medical monitoring and treatment device, a plurality of intrinsic heart beats prior to passage of a first interval, the plurality of intrinsic heart beats having an intrinsic frequency, the first interval being defined by an anti-tachyarrhythmic pacing rate, and applying, responsive to detecting the intrinsic frequency, a series of pacing pulses via the at least one therapy electrode, the series of pacing pulses having a frequency above the intrinsic frequency.

According to one embodiment, the identified cardiac condition includes an erratic heart rate, further comprising identifying a first series of heart beats within the information, the first series having a lower frequency, identify a second series of heart beats within the information, the second series having an upper frequency, and applying, responsive to identifying the erratic heart rate, a series of pacing pulses via the at least one therapy electrode, the series of pacing pulses having a frequency above the lower frequency and below the upper frequency. According to another embodiment, the identified cardiac condition includes at least one of asystole and pulseless electrical activity, further comprising determining that a first interval has passed without detection of a heart beat, and applying, responsive to determining that the first interval has passed, a pacing pulse via the at least one therapy electrode. According to another embodiment, the at least one pacing routine is further configured to apply a defibrillating shock via the at least one treatment electrode prior to applying the pacing pulse. According to one embedment, the method further comprises determining whether the at least one pacing routine resulted in capture, and adjusting, responsive to determining that capture did not result, the characteristics of pacing pulses applied during subsequent executions of the at least one pacing routine.

Still other aspects, embodiments, and advantages of these exemplary aspects and embodiments are discussed in detail below. Moreover, it is to be understood that both the foregoing information and the following detailed description are merely illustrative examples of various aspects and embodiments of the present invention, and are intended to provide an overview or framework for understanding the nature and character of the claimed aspects and embodiments. Any embodiment disclosed herein may be combined with any other embodiment in any manner consistent with at least one of the aspects disclosed herein, and references to "an embodiment," "some embodiments," "an alternate embodiment," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. The appearance of such terms herein is not necessarily all referring to the same embodiment.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
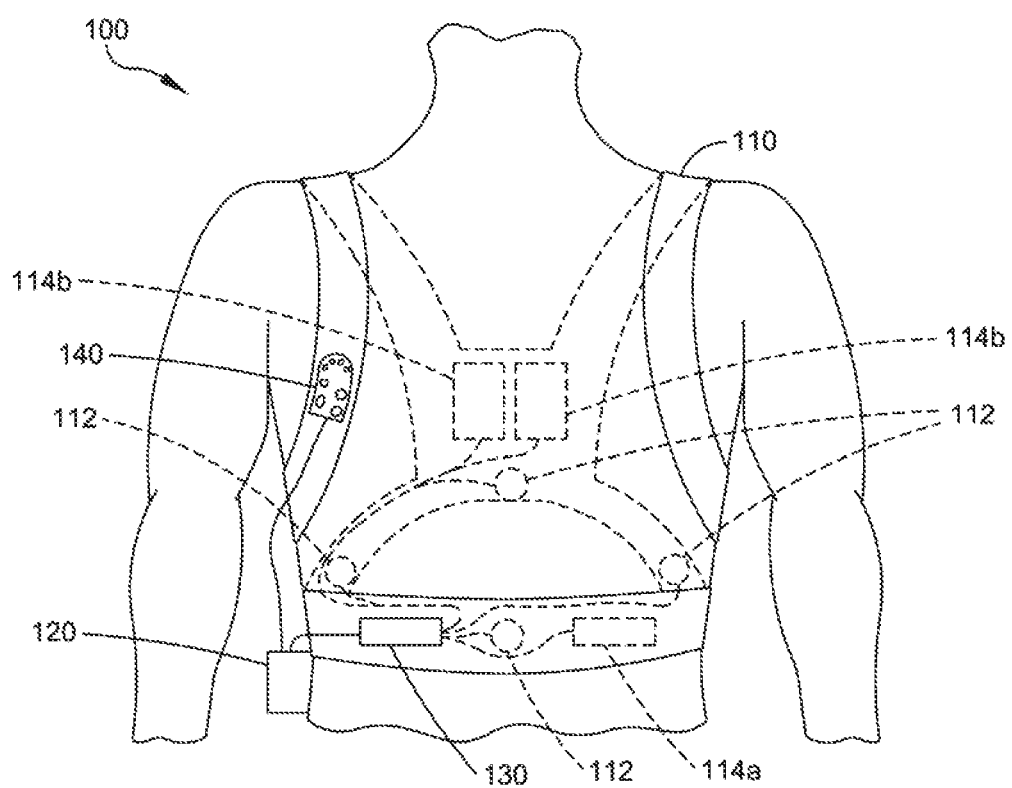
FIG. 1 illustrates a medical monitoring and treatment device, such as a wearable defibrillator.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

FIG. 1 illustrates a medical monitoring and treatment device, such as a LifeVest® Wearable Cardioverter Defibrillator available from ZOLL Medical Corporation of Chelmsford, Mass. As shown, the medical monitoring and treatment device 100 includes a harness 110 having a pair of shoulder straps and a belt that is worn about the torso of a patient. The harness 110 is typically made from a material, such as cotton, nylon, spandex, or antron that is breathable, and unlikely to cause skin irritation, even when worn for prolonged periods of time. The medical monitoring and treatment device 100 includes a plurality of electrocardiographic (ECG) sensing electrodes 112 that are disposed by the harness 110 at various positions about the patient's body and electrically coupled (wirelessly or by a wired connection) to a portable treatment controller 120 via a connection pod 130. The plurality of ECG sensing electrodes 112 are used by the portable treatment controller 120 to monitor the cardiac function of the patient and generally include a front/back pair of ECG sensing electrodes and a side/side pair of ECG sensing electrodes. It should be appreciated that additional ECG sensing electrodes may be provided, and the plurality of ECG sensing electrodes 112 may be disposed at varying locations about the patient's body. In addition, the plurality of ECG electrodes 112 may incorporate any electrode system, including conventional stick-on adhesive electrodes, dry-sensing capacitive ECG electrodes, radio transparent electrodes, segmented electrodes, or one or more long term wear electrodes that are configured to be continuously worn by a patient for extended periods (e.g., 3 or more days). One example of such a long term wear electrode is described in co-pending Application Ser. No. 61/653,749, titled "LONG TERM WEAR MULTIFUNCTION BIOMEDICAL ELECTRODE," filed May 31, 2012, which is hereby incorporated herein by reference in its entirety.

The medical monitoring and treatment devices disclosed herein may incorporate sundry materials arranged in a variety of configurations to maintain a proper fit with the patient's body. For example, some embodiments include a garment as described in co-pending application Ser. No. 13/460,250, titled "PATIENT-WORN ENERGY DELIVERY APPARATUS AND TECHNIQUES FOR SIZING SAME," filed Apr. 30, 2012, which is hereby incorporated herein by reference in its entirety. Thus embodiments are not limited to the configuration and materials described above with reference to FIG. 1.

The medical monitoring and treatment device 100 also includes a plurality of therapy electrodes 114 that are electrically coupled to the portable treatment controller 120 via the connection pod 130 and which are capable of delivering one or more therapeutic defibrillating shocks to the body of the patient, if it is determined that such treatment is warranted. As shown, the plurality of therapy electrodes 114 includes a first therapy electrode 114a that is disposed on the front of the patient's torso and a second therapy electrode 114b that is disposed on the back of the patient's torso. The second therapy electrode 114b includes a pair of therapy electrodes that are electrically coupled together and act as the second therapy electrode 114b. The use of two therapy electrodes 114a, 114b permits a biphasic shock to be delivered to the body of the patient, such that a first of the two therapy electrodes can deliver a first phase of the biphasic shock with the other therapy electrode acting as a return, and the other therapy electrode can deliver the second phase of the biphasic shock with the first therapy electrode acting as the return. The connection pod 130 electrically couples the plurality of ECG sensing electrodes 112 and the plurality of therapy electrodes 114 to the portable treatment controller 120, and may include electronic circuitry. For example, in one implementation the connection pod 130 includes signal acquisition circuitry, such as a plurality of differential amplifiers to receive ECG signals from different ones of the plurality of ECG sensing electrodes 112 and to provide a differential ECG signal to the portable treatment controller 120 based on the difference therebetween. The connection pod 130 may also include other electronic circuitry, such as a motion sensor or accelerometer by which patient activity may be monitored.

In some embodiments, both the first therapy electrode 114a and the second therapy electrode 114b are disposed on the front of the patient's torso. For example, the first therapy electrode 114a may be located at external to the apex of the heart and the second therapy electrode 114b may be located along the parasternal line. Thus embodiments are not limited to a particular arrangement of therapy electrodes 114.

In some embodiments, the plurality of ECG sensing electrodes 112 are positioned and paired such that artifacts generated from electrical activity are decreased. In other embodiments, the electronic circuitry included in the portable treatment controller 120 may equalize artifacts measured at electrodes by changing a gain or impedance. Other techniques of decreasing or preventing artifacts within measured electrical activity that may be used in conjunction the embodiments disclosed herein are explained in U.S. Pat. No. 8,185,199, titled "MONITORING PHYSIOLOGICAL SIGNALS DURING EXTERNAL ELECTRICAL STIMULATION," issued May 22, 2012, which is incorporated by reference herein in its entirety.

As shown in FIG. 1, the medical monitoring and treatment device 100 may also include a user interface pod 140 that is electrically coupled to the portable treatment controller 120. The user interface pod 140 can be attached to the patient's clothing or to the harness 110, for example, via a clip (not shown) that is attached to a portion of the interface pod 140. Alternatively, the user interface pod 140 may simply be held in a person's hand. The user interface pod 140 typically includes one or more actionable user interface elements (e.g., one or more buttons, a fingerprint scanner, a touch screen, microphone, etc. . . . ) by which the patient, or a bystander can communicate with the portable treatment controller 120, and a speaker by which the portable treatment controller 120 may communicate with the patient or the bystander. In certain models of the LifeVest® Wearable Cardioverter Defibrillator, the functionality of the user interface pod 140 is incorporated into the portable treatment controller 120.

Where the portable treatment controller 120 determines that the patient is experiencing cardiac arrhythmia, the portable treatment controller 120 may issue an audible alarm via a loudspeaker (not shown) on the portable treatment controller 120 and/or the user interface pod 140 alerting the patient and any bystanders to the patient's medical condition. Examples of notifications issued by the portable treatment controller 120 are described in co-pending application Ser. No. 13/428,703, titled "SYSTEM AND METHOD FOR ADAPTING ALARMS IN A WEARABLE MEDICAL DEVICE," filed Mar. 23, 2012, which is incorporated by reference herein in its entirety. The portable treatment controller 120 may also instruct the patient to press and hold one or more buttons on the portable treatment controller 120 or on the user interface pod 140 to indicate that the patient is conscious, thereby instructing the portable treatment controller 120 to withhold the delivery of one or more therapeutic defibrillating shocks. If the patient does not respond, the device may presume that the patient is unconscious, and proceed with the treatment sequence, culminating in the delivery of one or more defibrillating shocks to the body of the patient.

The portable treatment controller 120 generally includes at least one processor, microprocessor, or controller, such as a processor commercially available from companies such as Texas Instruments, Intel, AMD, Sun, IBM, Motorola, Freescale and ARM Holdings. In one implementation, the at least one processor includes a power conserving processor arrangement that comprises a general purpose processor, such as an Intel® PXA270 processor and a special purpose processor, such as a Freescale™ DSP56311 Digital Signal Processor. Such a power conserving processor arrangement is described in co-pending application Ser. No. 12/833,096, titled SYSTEM AND METHOD FOR CONSERVING POWER IN A MEDICAL DEVICE, filed Jul. 9, 2010 (hereinafter the "'096 application") which is incorporated by reference herein in its entirety. The at least one processor of the portable treatment controller 120 is configured to monitor the patient's medical condition, to perform medical data logging and storage, and to provide medical treatment to the patient in response to a detected medical condition, such as cardiac arrhythmia.

Although not shown, the medical monitoring and treatment device 100 may include additional sensors, other than the ECG sensing electrodes 112, capable of monitoring the physiological condition or activity of the patient. For example, sensors capable of measuring blood pressure, heart rate, heart sounds, thoracic impedance, pulse oxygen level, respiration rate, and the activity level of the patient may also be provided.

Figure 2:
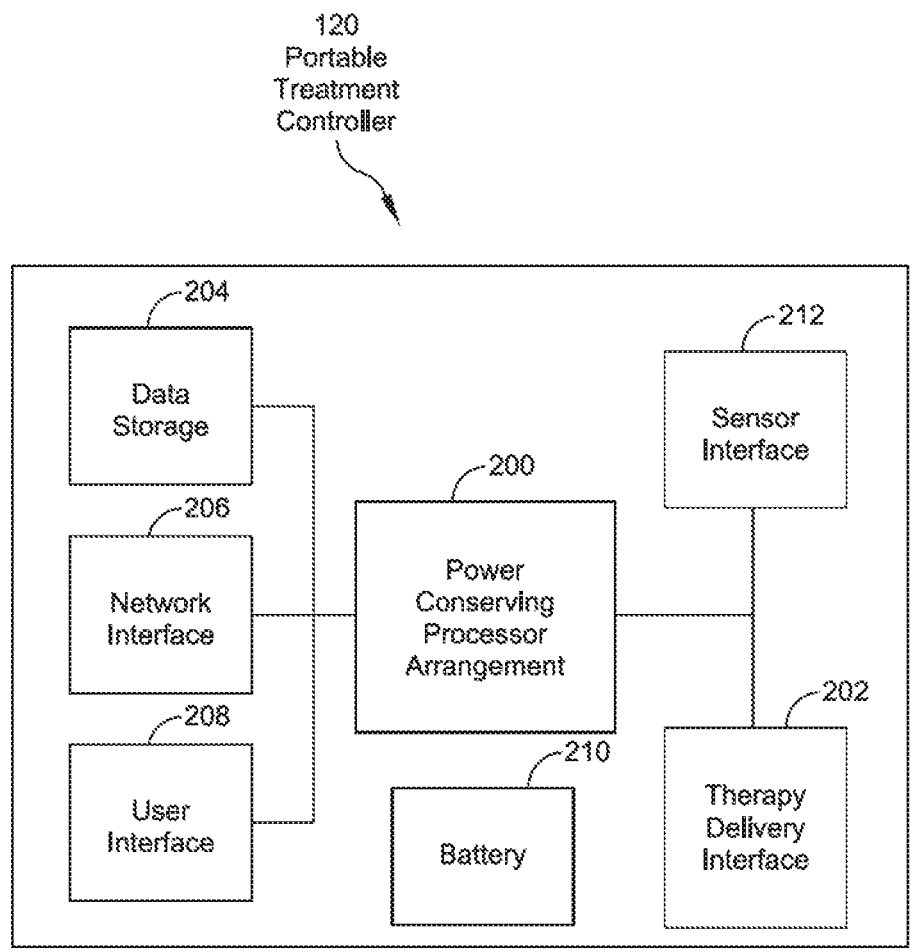
FIG. 2 is a functional block diagram of one example of a portable treatment controller that may be used in the medical monitoring and treatment device of FIG. 1.

FIG. 2 illustrates a portable treatment controller 120 that is configured to perform the critical functions of monitoring physiological information for abnormalities and initiating treatment of detected abnormalities. As shown, the portable treatment controller 120 can include the power conserving processor arrangement 200 described in the '096 application, a sensor interface 212, a therapy delivery interface 202, data storage 204, a communication network interface 206, a user interface 208 and a battery 210. In this illustrated example, the battery 210 is a rechargeable 3 cell 2200 mAh lithium ion battery pack that provides electrical power to the other device components with a minimum 24 hour runtime between charges. Such a battery 210 has sufficient capacity to administer one or more therapeutic shocks and the therapy delivery interface 202 has wiring suitable to carry the load to the therapy electrodes 114. Moreover, in the example shown, the battery 210 has sufficient capacity to deliver up to 5 or more therapeutic shocks, even at battery runtime expiration. The amount of power capable of being delivered to a patient during a defibrillating shock is substantial, for example up to approximately 200 Joules.

The sensor interface 212 and the therapy delivery interface 202 are coupled to the power conserving processor arrangement 200 and more particularly to the critical purpose processor of the power conserving processing arrangement 200 as described in the '096 application. The data storage 204, the network interface 206, and the user interface 208 are also coupled to the power conserving processor arrangement 200, and more particularly to the general purpose processor of the power conserving processing arrangement as also described in the '096 application.

In the example shown, the data storage 204 includes a computer readable and writeable nonvolatile data storage medium configured to store non-transitory instructions and other data. The medium may, for example, be optical disk, magnetic disk or flash memory, among others and may be permanently affixed to, or removable from, the portable treatment controller 120.

As shown in FIG. 2, the portable treatment controller 120 includes several system interface components 202, 206 and 212. Each of these system interface components is configured to exchange, i.e., send or receive data, with specialized devices that may be located within the portable treatment controller 200 or elsewhere. The components used by the interfaces 202, 206 and 212 may include hardware components, software components or a combination of both. In the instance of each interface, these components physically and logically couple the portable treatment controller 200 to one or more specialized devices. This physical and logical coupling enables the portable treatment controller 120 to both communicate with and, in some instances, control the operation of specialized devices. These specialized devices may include physiological sensors, therapy delivery devices, and computer networking devices.

According to various examples, the hardware and software components of the interfaces 202, 206 and 212 employ a variety of coupling and communication techniques. In some examples, the interfaces 202, 206 and 212 use leads, cables or other wired connectors as conduits to exchange data between the portable treatment controller 120 and specialized devices. In other examples, the interfaces 202, 206 and 212 communicate with specialized devices using wireless technologies such as radio frequency or infrared technology. The software components included in the interfaces 202, 206 and 212 enable the power conserving processor arrangement 200 to communicate with specialized devices. These software components may include elements such as objects, executable code and populated data structures. Together, these hardware and software components provide interfaces through which the power conserving processor arrangement 200 can exchange information with the specialized devices. Moreover, in at least some examples where one or more specialized devices communicate using analog signals, the interfaces 202, 206 and 212 can include components configured to convert analog information into digital information, and vice-versa.

As discussed above, the system interface components 202, 206 and 212 shown in the example of FIG. 2 support different types of specialized devices. For instance, the components of the sensor interface 212 couple the power conserving processor arrangement 200 to one or more physiological sensors such as a body temperature sensors, respiration monitors and dry-capacitive ECG sensing electrodes. It should be appreciated that other types of ECG sensing electrodes may be used, as the present invention is not limited to any particular type of ECG sensing electrode. The components of the therapy delivery interface 202 couple one or more therapy delivery devices, such as capacitors and defibrillator electrodes, to the power conserving processor arrangement 200. In addition, the components of the network interface 206 couple the power conserving processor arrangement to a computer network via a networking device, such as a bridge, router or hub. The network interface 206 may supports a variety of standards and protocols, examples of which include USB, TCP/IP, Ethernet, Wireless Ethernet, Bluetooth, ZigBee, M-Bus, IP, IPV6, UDP, DTN, HTTP, FTP, SNMP, CDMA, NMEA and GSM. To ensure data transfer is secure, in some examples, the portable treatment controller 200 can transmit data via the network interface 206 using a variety of security measures including, for example, TSL, SSL or VPN. In other examples, the network interface 206 includes both a physical interface configured for wireless communication and a physical interface configured for wired communication.

The user interface 208 shown in FIG. 2 includes a combination of hardware and software components that allow the portable treatment controller 200 to communicate with an external entity, such as a user. These components are configured to receive information from actions such as physical movement, verbal intonation or thought processes. In addition, the components of the user interface 208 can provide information to external entities. Examples of the components that may be employed within the user interface 208 include keyboards, mouse devices, trackballs, microphones, electrodes, touch screens, printing devices, display screens and speakers.

The LifeVest® wearable cardioverter defibrillator can monitor a patient's ECG signals, detect various cardiac arrhythmias, and provide life saving defibrillation treatment to a patient suffering a treatable form of cardiac arrhythmia such as Ventricular Fibrillation (VF) or Ventricular Tachycardia (VT).

Applicants have appreciated that such a medical monitoring and treatment device can be configured to perform a variety of different types of cardiac pacing to treat a wide variety of different cardiac arrhythmias, such as bradycardia, tachycardia, an irregular cardiac rhythm, or asystole. Applicants have further appreciated that, in other embodiments, a medical monitoring and treatment device can be configured to perform pacing to treat pulseless electrical activity. In accordance with an aspect of the present invention, the device can be configured to pace the heart of the patient at a fixed energy level and pulse rate, to pace the heart of the patient on demand with a fixed energy level and an adjustable rate responsive to the detected intrinsic activity level of the patient's heart, or to pace the heart of the patient using capture management with an adjustable energy level and rate responsive to the detected intrinsic activity level of the patient's heart and the detected response of the patient's heart. The various types of pacing may be applied to the patient externally by one or more of the therapy electrodes 114a, 114b (FIG. 1). Various types of pacing that can be performed by a medical monitoring and treatment device, such as the LifeVest® wearable cardioverter defibrillator, can include asynchronous pacing at a fixed rate and energy, pacing on demand at a variable rate and fixed energy, and capture management pacing with an adjustable rate and adjustable energy level.

In some embodiments, the medical monitoring and treatment device is configured to periodically assess the level of discomfort of the patient during pacing operation. In these embodiments, responsive to determining that the patient's discomfort level exceeds a threshold, the device attempts to adjust the attributes of the pacing activity to lessen the discomfort experienced by the patient.

In one embodiment, the medical monitoring and treatment device provides a user interface through which the device receives information descriptive of the discomfort level experienced by a patient. Should this information indicate that the level of discomfort has transgressed a threshold level, the device adjusts characteristics of the pacing operation in an attempt to decrease the level of discomfort.

In another embodiment, the medical monitoring and treatment device assesses the level of discomfort of the patient by monitoring and recording the patient's movement before, during, and after administration of a pacing pulse. The device may monitor the patient's movement using a variety of instrumentation including, for example, one or more accelerometers, audio sensors, etc. To assess the level of discomfort experienced by the patient during pacing pulses, the device may analyze the recorded history of the patient's movement and identify correlations between changes in the patient's movement and the pacing pulse. Strong correlations between pacing pulses and sudden patient movement, which may be representative of a flinch, and strong correlations between pacing pulses and a sudden stoppage of movement, may indicate that a patient is experiencing discomfort. Correlations having a value that transgresses a threshold value may be deemed to indicate discomfort and may cause the device to adjust the characteristics of a pacing pulse.

In other embodiments, the device adjusts the characteristics of the pacing operation to lessen the discomfort level of the patient. The characteristics of the pacing operation that may be adjusted include, for example, the energy level of pacing pulses, the width of the pacing pulses, and the rate of the pacing pulses. In some embodiments, the device monitors the cardiac activity of the patient during this adjustment process to ensure that the pacing operation continues to effectively manage cardiac function. In these embodiments, the device may revert the characteristics of the pacing operation to their previous settings, should the pacing operation become ineffective.

1. Fixed Rate and Energy Pacing

Figure 3:
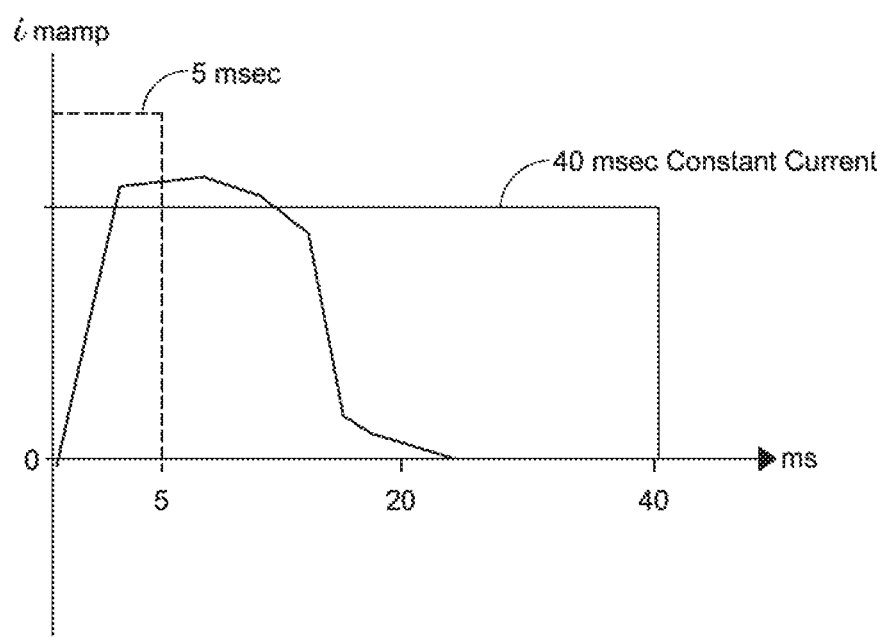
FIG. 3 illustrates a number of different pacing waveforms that may be provided by the medical monitoring and treatment device, including a 40 ms constant current pulse.

In accordance with an aspect of the present invention, a medical monitoring and treatment device, such as the LifeVest® wearable cardioverter defibrillator, can be configured to pace the heart of a patient at a fixed rate and fixed energy in response to various types of cardiac arrhythmias. Examples of these cardiac arrhythmias include bradyarrythmia, a lack of sensed cardiac activity (spontaneous or post shock asystole) and pulseless electrical activity. In some cases, these cardiac arrhythmias may occur before or after one or more defibrillation shocks. For example, the device may be configured to provide pulses at a fixed energy level, a fixed pulse width, and a fixed frequency in response to detection of any of the above-noted events by the ECG sensing electrodes 112. The energy level of the pacing pulses may be set to a fixed value by applying a desired current waveform for a determined duration of time by one or more of the therapy electrodes 114a, 114b. The maximum current level of the current waveform may be set to a value between approximately 0 mAmps to 200 mAmps, the pulse width may be set to a fixed value between approximately 0.05 ms to 2 ms, and the frequency of the pulses may be set to a fixed value between approximately 30 pulses per minute (PPM) to approximately 200 PPM. In accordance with one embodiment, a 40 ms square wave pulse is used. Exemplary pacing current waveforms, including a 40 ms constant current pulse, a 5 ms constant current pulse, and a variable current pulse are shown in FIG. 3.

During pacing operation of the medical monitoring and treatment device, the device may periodically pause for a period of time to evaluate the patient via the ECG sensing electrodes to determine whether a normal sinus rhythm has returned. Where the device detects a normal sinus rhythm, the device may discontinue the application of pacing pulses and simply continue monitoring the patient's physiological signals, such as the patient's ECG, temperature, pulse oxygen level, etc.

During an initial fitting of the medical monitoring and treatment device, the level of current, the pulse width, and the frequency of the pulses may be set to an appropriate level based on the input of a medical professional (such as the patient's cardiologist) and the physiological condition of the patient (e.g., based on the patient's normal resting heart rate, the patient's thoracic impedance, etc.) Alternatively, the level of current, the pulse width, and the frequency of the pulses may simply be set to an appropriate value based on typical impedance values for an adult or child, and typical resting heart rates for an adult or child.

It should be appreciated that because pacing at a fixed rate may interfere with the patient's own intrinsic heart rate, the device can be configured to perform such fixed rate and energy pacing only in the event of a life-threatening Bradyarrythmia, a lack of any detected cardiac activity following shock, or in response to pulseless electrical activity following shock.

2. Demand (Adjustable Rate) Pacing

In accordance with an aspect of the present invention, a medical monitoring and treatment device, such as the LifeVest® wearable cardioverter defibrillator, can also be configured to pace the heart of a patient at a variable rate and a fixed energy in response to various types of cardiac arrhythmias, including a bradyarrythmia (i.e., an excessively slow heart rate), tachycardia (i.e., an excessively fast heart rate), an erratic heart rate with no discernible regular sinus rhythm, a lack of sensed cardiac activity (asystole), and pulseless electrical activity. Some of these cardiac arrhythmias may occur following one or more defibrillation shocks.

As known to those skilled in the art, pacing at a fixed rate and energy may not be appropriate to the particular type of cardiac arrhythmia of the patient, and even where the rate and energy level is appropriate, pacing at a fixed rate can result in competition between the rate at which the pacing pulses are being applied and the intrinsic rhythm of the patient's heart. For example, pacing at a fixed rate may result in the application of a pacing pulse during the relative refractory period of the normal cardiac cycle (a type of R wave on a T wave effect) that could promote ventricular tachycardia or ventricular fibrillation. To overcome some of the disadvantages of fixed rate and energy pacing, the medical monitoring and treatment device can be configured to perform demand pacing, wherein the rate of the pacing pulses may be varied dependent on the physiological state of the patient. For example, during demand pacing, the device can deliver a pacing pulse only when needed by the patient. In general, during the demand mode of pacing, the device searches for any intrinsic cardiac activity of the patient, and if a heart beat is not detected within a designated interval, a pacing pulse is delivered and a timer is set to the designated interval. Where the designated interval expires without any detected intrinsic cardiac activity of the patient, another pacing pulse is delivered and the timer reset. Alternatively, where an intrinsic heart beat of the patient is detected within the designated interval, the device resets the timer and continues to search for intrinsic cardiac activity.

Figure 4:
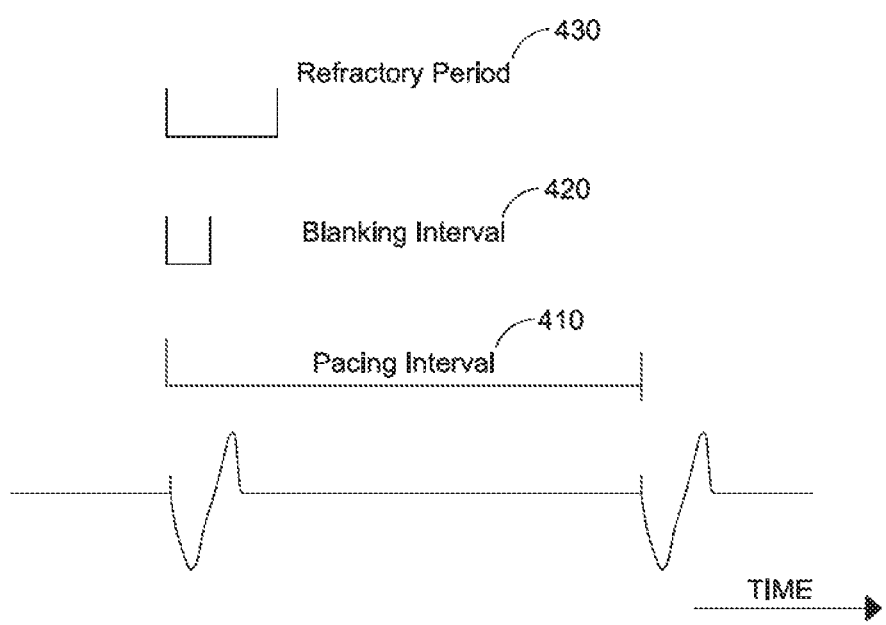
FIG. 4 illustrates various aspects of demand pacing which can be adjusted in connection with on demand pacing or capture management pacing.

FIG. 4 helps to illustrate some of the aspects of demand pacing and the manner in which demand pacing can be performed by the medical monitoring and treatment device. As illustrated in FIG. 4, the device may have a variable pacing interval 410 corresponding to the rate at which pacing pulses are delivered to the patient in the absence of any detected intrinsic cardiac activity detected by the ECG sensing electrodes 112 and ECG monitoring and detection circuitry. For example, the rate at which pulsing paces are to be delivered to the patient (referred to as the "base pacing rate" herein) may be set at 60 PPM and therefore, the corresponding base pacing interval 410 would be set to 1 second.

The medical monitoring and treatment device may also have a hysteresis rate (not shown in FIG. 4) corresponding to the detected intrinsic heart rate of the patient below which the device performs pacing. According to some embodiments, the hysteresis rate is a configurable parameter that is expressed as a percentage of the patient's intrinsic heart rate. In the above example, the hysteresis rate may correspond to 50 beats per minute (BPM). In this example, if the intrinsic heart rate of the patient fell to 50 BPM or below (e.g., more than approximately 1.2 seconds between detected beats), the device would generate and apply a pacing impulse to the patient.

During application of a pacing pulse to the body of a patient and a short time thereafter, the medical monitoring and treatment device may intentionally blank out a portion of the ECG signals being received by the ECG monitoring and detection circuitry to prevent this circuitry (e.g., amplifiers, A/D converters, etc.) from being overwhelmed (e.g., saturated) by the pacing pulse. This may be performed in hardware, software, or a combination of both. This period of time, referred to herein as "the blanking interval" 420 may vary (e.g., between approximately 30 ms to 200 ms), but is typically between approximately 40 ms to 80 ms in duration.

In addition to the blanking interval 420, the medical monitoring and treatment device can have a variable refractory period 430 that may vary dependent upon the base pacing rate. The refractory period 430 corresponds to a period of time in which signals sensed by the ECG sensing electrodes 112 and the ECG monitoring and detection circuitry are ignored, and includes the blanking interval. The refractory period 430 allows any generated QRS complexes or T waves induced in the patient by virtue of the pacing pulse to be ignored, and not interpreted as intrinsic cardiac activity of the patient. For example, where the base pacing rate is set to below 80 PPM, the refractory period might correspond to 340 ms, and where the base pacing rate is set above 90 PPM, the refractory period might correspond to 240 ms. For typical applications, the refractory period is generally between about 150 ms and 500 ms.

In accordance with an aspect of the present invention, the sensitivity of the ECG monitoring and detection that is performed by the medical monitoring and treatment device may also be varied to adjust the degree by which the ECG sensing electrodes and associated ECG monitoring and detection circuitry can detect the patient's intrinsic cardiac activity. For example, where the amplitude of certain discernable portions (e.g., an R-wave) of a patient's intrinsic ECG signal is below that typically encountered, the voltage threshold over which this discernable portion can be detected as belonging to an ECG signal (and not attributed to noise or other factors) may be lowered, for example from 2.5 mV to 1.5 mV, to better detect the patient's intrinsic cardiac activity. For instance, during an initial fitting of the medical monitoring and treatment device, the sensitivity threshold of the device may be reduced to a minimal value (e.g., 0.4 mV) and the patient's intrinsic ECG signals may be monitored. The sensitivity threshold may then be incrementally increased (thereby decreasing the sensitivity of the device) and the patient's intrinsic ECG signals monitored until these ECG signals are no longer sensed. The sensitivity threshold may then be incrementally decreased (thereby increasing the sensitivity of the device) until the patient's intrinsic ECG signals are again sensed, and the sensitivity threshold of the device may be set to approximately half this value.

As with fixed energy and rate pacing, the device may be configured to provide pulses at a fixed energy level and a fixed pulse width in response to detection of any of the above-noted events by the ECG sensing electrodes 112 and the ECG monitoring and detection circuitry. The maximum current level of the current waveform may be set to a value between approximately 10 mAmps to 200 mAmps, the pulse width may be set to a fixed value between approximately 20 ms to 40 ms, and the base rate of the pulses may be set to a fixed value between approximately 30 pulses per minute (PPM) to approximately 200 PPM, although the actual rate of the pacing pulses can vary based upon the intrinsic cardiac activity of the patient. In accordance with one embodiment, a 40 ms constant current pulse is used, and the current level is set to a fixed value based upon the input of a medical professional, such as the patient's cardiologist and the physiological condition of the patient. The base pacing rate and the hysteresis rate may also be set based upon the input of the patient's cardiologist (or other medical professional) and the physiological condition of the patient, and the blanking interval and refractory period set to an appropriate time interval based upon the base pacing rate and/or the hysteresis rate.

Although the base pacing rate may be set to a particular value based on the physiological condition of the patient and input from a medical profession, the medical monitoring and treatment device can include a number of different pacing routines to respond to different cardiac arrhythmias, such as bradycardia, tachycardia, an erratic heart rate with no discernable regular sinus rhythm, asystole, or pulseless electrical activity. These pacing routines may be implemented using a variety of hardware and software components and embodiments are not limited to a particular configuration of hardware or software. For instance, the pacing routines may be implemented using an application-specific integrated circuit (ASIC) tailored to perform the functions described herein.

A. Bradycardia

As discussed above, where Bardycardia is detected and the intrinsic cardiac rate of the patient is below that of the hysteresis rate, the medical monitoring and treatment device will pace the patient at the pre-set base pacing rate. During this time, the device will continue to monitor the patient's intrinsic heart rate and will withhold pacing pulses in the event that an intrinsic heart beat is detected within designated interval corresponding to the hysteresis rate. This type of on demand pacing is frequently termed "maintenance pacing."

B. Tachycardia

For responding to tachycardia, the medical monitoring and treatment device may additionally include another pacing rate, termed an "anti-tachyarrhythmic pacing rate" herein, above which the device will identify that the patient is suffering from tachycardia, and will pace the patient in a manner to bring the patient's intrinsic heart back toward the base racing rate. For example, the device may employ a technique known as overdrive pacing wherein a series of pacing pulses (e.g., between about 5 and 10 pacing pulses) are delivered to the patient at a frequency above the intrinsic rate of the patient in an effort to gain control of the patient's heart rate. Once it is determined that the device is in control of the patient's heart rate, the rate (i.e., the frequency) of the pulses may be decremented, for example by about 10 ms, and another series of pacing pulses delivered. This delivery of pulses and the decrease in frequency may continue until the detected intrinsic cardiac rate of the patient is below the anti-tachyarrhythmic pacing rate, or at the base pacing rate. This type of pacing is frequently termed "overdrive pacing" or "fast pacing."

C. Erratic Heart Rate

For responding to an erratic heart rate, the medical monitoring and treatment device may perform a type of pacing that is similar to a combination of maintenance pacing and overdrive pacing discussed above. For example, where the medical monitoring and treatment device detects an erratic heart rate with no discernable sinus rhythm, the device may deliver a series of pacing pulses (e.g., between about 5 and 10 pacing pulses) to the patient at a particular frequency. This frequency may be one that is above a lower frequency of a series of detected intrinsic beats of the patient's heart and below an upper frequency of the detected intrinsic beats of the patient's heart. After delivering the series of pulses, the device may monitor the patient's heart to determine if it has synchronized to the rate of the series of delivered pulses. Where the intrinsic rate of the patient's heart is still erratic, the device may increase the frequency of the series of pulses and deliver another series. This may continue until it is established that the patient's heart is now in a more regular state. Upon determining that the patient's heart is now in a more regular state, the device may perform maintenance pacing if it is determined that the patient's intrinsic heart rate is too low as discussed in section 2A above, or perform pacing at a decremented rate in the manner discussed in section 2B above, if such is warranted.

D. Asystole or Pulseless Electrical Activity

For responding to asystole or a detected condition of pulseless electrical activity, the medical monitoring and treatment device may perform maintenance pacing similar to that described in section 2A above. This type of pacing would be performed after a series of one or more defibrillating shocks that attempt to restore a normal sinus rhythm to the heart of the patient.

In each of the above types of pacing, the medical monitoring and treatment device may be configured to perform a particular type of pacing only after a programmable delay after such cardiac arrhythmias are detected, or after a programmable period of time after one or more defibrillating shocks are delivered.

3. Capture Management

In accordance with an aspect of the present invention, a medical monitoring and treatment device, such as the LifeVest® wearable cardioverter defibrillator, can also be configured to pace the heart of a patient using capture management with an adjustable energy level and an adjustable rate in response to various types of cardiac arrhythmias. The various types of cardiac arrhythmias can include a bradycardia, tachycardia, an erratic heart rate with no discernable regular sinus rhythm, a lack of sensed cardiac activity (asystole) following or independent of one or more defibrillation shocks, a life-threatening Bradyarrythmia following one or more defibrillation shocks, or pulseless electrical activity following one or more defibrillation shocks.

As known to those skilled in the art, capture management refers to a type of pacing in which the energy level of pacing pulses and the rate of delivery of those pacing pulses may be varied based upon the detected intrinsic activity level of the patient's heart and the detected response of the patient's heart to those pacing pulses. In cardiac pacing, the term "capture" is used to refer to the response of a patient's heart to a pulse of energy which results in ventricular depolarization. In cardiac pacing, it is desirable to limit the amount of energy in each pulse to a minimal amount required for capture; thereby minimizing the amount of discomfort associated with external pacing.

In general, the manner in which the medical monitoring and treatment device can perform capture management pacing is similar to that of demand pacing described above, in that it may adjust the rate at which pacing pulses are delivered based upon the detected intrinsic rate of cardiac activity of the patient. The sensitivity of the device to the patient's ECG may be adjusted in a similar manner to that described above with respect to demand pacing. Further, capture management pacing may be used to treat the same types of cardiac arrhythmias as the demand pacing described above, such as bradycardia, tachycardia, an erratic heart rate with no discernable sinus rhythm, asystole, or pulseless electrical activity.

However, in contrast to a device that performs demand pacing, a device that is configured to perform capture management pacing will typically have a refractory period 430 (see FIG. 4) that is significantly shorter than a device configured to perform demand pacing. Indeed, when using capture management pacing, there may be no refractory period 430 at all, but only a blanking interval 420. Alternatively, where there is a refractory period 430, the refractory period 430 may be similar in duration to the blanking interval 420. As would be appreciated by those skilled in the art, this is because during capture management pacing, the response of the patient's heart is monitored by the ECG sensing electrodes 112 and ECG monitoring and detection circuitry to detect whether the delivered pulse of energy resulted in capture. For this reason, while the ECG monitoring and detection circuitry may be switched off or effectively disabled during the delivery of energy pulses, it is important that it be switched back on or otherwise enabled shortly thereafter to detect whether the delivered pulse resulted in capture. In one embodiment in which a 40 ms constant current pulse is used, the blanking interval 420 may be set to approximately 45 ms to avoid saturation of the ECG monitoring and detection circuitry, but ensure that any intrinsic electrical activity of the patient's heart that was induced by the pacing pulse is detected.

During capture management pacing, the medical monitoring and treatment device can deliver a pulse of energy at a determined energy level and monitor the patient's response to determine if capture resulted. Where it is determined that the delivered pulse did not result in capture, the energy level of the next pulse may be increased. For example, where the device is a medical monitoring and treatment device that is external to the patient, the initial setting may be configured to provide a 40 ms rectilinear and constant current pulse of energy at a current of 40 mAmps, and increase the amount of current in increments of 2 mAmps until capture results. The next pacing pulse may be delivered at increased current relative to the first pacing pulse and at a desired rate relative to the first pacing pulse in the absence of any detected intrinsic cardiac activity of the patient. Where the next pacing pulse does not result in capture, the energy may be increased until capture is detected. The medical monitoring and treatment device may then continue pacing at this energy level and at a desired rate in the absence of any detected intrinsic cardiac activity of the patient. During this period of time, the device monitors the patient's cardiac response to the pacing pulses, and may increment the energy level further, should it be determined over one or more subsequent pulses that capture did not result.

In an alternative configuration, the medical monitoring and treatment device may apply a series of pulses at an initial energy level and rate, and monitor the patient's response to determine if capture resulted. Where capture did not result, or where capture resulted in response to some of the pulses, but not all, the device may increase the energy of a next series of pulses until capture results for each pulse.

Alternatively, the device may be configured to identify a minimum amount of energy that results in capture during capture management pacing. Where it is determined that the delivered pulse did result in capture, the energy level of the next pulse may be decreased. For example, where the device is a medical monitoring and treatment device that is external to the patient, the initial setting may be configured to provide a 40 ms constant current pulse of energy at a current of 70 mAmps Where it is determined that the delivered pulse resulted in capture, subsequent pacing pulses may be delivered and decreased in increments of 5 mAmps and at a desired rate relative to the first pacing pulse in the absence of any detected intrinsic cardiac activity of the patient until capture is no longer achieved. Where the next pacing pulse does not result in capture, the energy setting may be increased to the last current known to produce a pulse resulting in capture, and then delivering a pulse at the higher energy setting, thus delivering the minimal amount of energy required for capture. The medical monitoring and treatment device may then continue pacing at this energy level and at a desired rate in the absence of any detected intrinsic cardiac activity of the patient. During this period of time, a similar routine may be re-performed at predetermined intervals to ensure that the minimum amount of energy is being delivered for capture. In addition, during this period of time, the device monitors the patient's cardiac response to the pacing pulses, and may increase the energy level should it be determined over one or more subsequent pulses that capture did not result.

It should be appreciated that in the various embodiments described above, an external medical monitoring and treatment device has been described which may not only provide life saving defibrillation or cardioversion therapy, but may also provide a wide variety of different pacing regimens. Because the medical monitoring and treatment device can monitor a patient's intrinsic cardiac activity, the patient's thoracic impedance, and other physiological parameters of the patient, the device may be configured to recommend various settings to a medical professional for review and approval. The various settings that may be recommended may include a recommended base pacing rate, a recommended hysteresis rate, a recommended anti-tachyarrhythmic pacing rate, a recommended energy level (or initial energy level if capture management is used), a recommended blanking interval, and/or refractory period, and a recommended sensitivity threshold. In the case of a medical monitoring and treatment device such as the LifeVest® cardioverter defibrillator, this initial recommendation may be performed when the patient is being fitted for and trained on the use of the device.

Although the ability to recommend such settings to a medical professional for their review and approval is particularly well suited to a medical monitoring and treatment device, such as the LifeVest® cardioverter defibrillator, such functionality could also be implemented in an Automated External Defibrillator (AED) or an Advanced Life Support (ALS) type of defibrillator, such as the M Series defibrillator, R Series ALS defibrillator, R Series Plus defibrillator, or E Series defibrillator manufactured by the ZOLL Medical Corporation of Chelmsford Mass. It should be appreciated that monitoring the patient's intrinsic cardiac activity and other physiological parameters and making recommendations to a trained medical professional for their review and approval (or possible modification) could reduce the amount of time that is spent manually configuring such devices prior to use on the patient.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A non-invasive ambulatory medical monitoring and treatment device comprising:
  a garment worn about a torso of a patient;
  at least one therapy electrode disposed in the garment and configured to be in contact with the patient's skin;
  a plurality of ECG sensing electrodes disposed in the garment at a plurality of locations on the patient's body;

a memory storing ECG information indicative of the patient's cardiac activity, the ECG information obtained from the plurality of ECG sensing electrodes;

circuitry for implementing a plurality of pacing routines, each pacing routine of the plurality of pacing routines corresponding to at least one cardiac condition of a plurality of cardiac conditions; and at least one processor coupled to the circuitry and configured to:
identify, within the ECG information, at least one cardiac condition of the plurality of cardiac conditions; and
respond to the identified cardiac condition in part by causing execution of at least one pacing routine corresponding to the identified cardiac condition.

2. The device of claim 1, wherein the identified cardiac condition includes bradycardia and the at least one pacing routine is configured to:
determine that a first interval has passed without detection of a heart beat; and apply, responsive to determining that the first interval has passed, a pacing pulse via the at least one therapy electrode.

3. The device of claim 2, wherein the first interval is based on at least one of a base pacing rate and a hysteresis rate.

4. The device of claim 3, wherein the at least one pacing routine is further configured to:
detect an intrinsic heart beat prior to passage of a second interval;
determine a third interval based on the base pacing rate, the hysteresis rate, and a point where the intrinsic heart beat was detected; and
determine whether another intrinsic heart beat occurs within the third interval.

5. The device of claim 1, wherein the identified cardiac condition includes tachycardia and the at least one pacing routine comprises an anti-tachyarrhythmic pacing routine.

6. The device of claim 1, wherein the identified cardiac condition includes an erratic heart rate and the at least one pacing routine is configured to:
identify a first series of heart beats within the ECG information, the first series having a lower frequency;
identify a second series of heart beats within the ECG information, the second series having an upper frequency; and
apply, responsive to identifying the erratic heart rate, a series of pacing pulses via the at least one therapy electrode, the series of pacing pulses having a frequency above the lower frequency and below the upper frequency.

7. The device of claim 1, wherein the identified cardiac condition includes at least one of asystole and pulseless electrical activity and the at least one pacing routine is configured to:
determine that a first interval has passed without detection of a heart beat; and
apply, responsive to determining that the first interval has passed, a pacing pulse via the at least one therapy electrode.

8. The device of claim 7, wherein the at least one pacing routine is further configured to apply a defibrillating shock prior to applying the pacing pulse.

9. The device of claim 1, wherein the at least one pacing routine is further configured to:
determine whether the at least one pacing routine resulted in capture; and adjust, responsive to determining that capture did not result, the characteristics of pacing pulses applied during subsequent executions of the at least one pacing routine.

10. The device of claim 1, wherein the at least one pacing routine is further configured to:
determine whether the at least one pacing routine resulted in capture; and
adjust, responsive to determining that capture did result, the characteristics of pacing pulses applied during subsequent executions of the at least one pacing routine.

11. The device according to claim 10, wherein the characteristics of the pacing pulses subject to adjustment include a pulse energy level, a pulse rate, and a pulse width.

12. A method of treating cardiac dysfunction using a non-invasive ambulatory medical monitoring and treatment device having at least one treatment electrode and implementing a plurality of pacing routines, the method comprising:
monitoring, by the non-invasive ambulatory medical monitoring and treatment device, information indicative of a patient's cardiac condition;
identifying, by the non-invasive ambulatory medical monitoring and treatment device, within the information a cardiac condition from a plurality of cardiac conditions; and
responding to the identified cardiac condition at least in part by executing, by the non-invasive ambulatory medical monitoring and treatment device, at least one pacing routine of the plurality of pacing routines, the at least one pacing routine associated with the identified cardiac condition.

13. The method of claim 12, wherein the identified cardiac condition includes at least one of bradycardia and asystole.

14. A non-invasive ambulatory medical monitoring and treatment device comprising:
at least one therapy electrode;
at least one ECG sensing electrode;
a memory storing ECG information indicative of a patient's cardiac activity, the ECG information obtained from the at least one ECG sensing electrode;
circuitry for implementing at least one pacing routine corresponding to a cardiac condition; and
at least one processor coupled to the circuitry and configured to:
identify, within the ECG information, the cardiac condition;
execute the at least one pacing routine corresponding to the identified cardiac condition, the at least one pacing routine including at least one pacing pulse to be applied via the at least one therapy electrode;
determine whether the at least one pacing routine resulted in capture at least in part based on the ECG information; and
adjust, responsive to determining that capture did not result, at least one characteristic of at least one pacing pulse applied during subsequent execution of the at least one pacing routine.

15. The device of claim 14, wherein the identified cardiac condition includes at least one of bradycardia, tachycardia, erratic heart rate, asystole, and pulseless electrical activity.

16. The device of claim 14, wherein the at least one processor is further configured to:
adjust, responsive to determining that capture did result, the characteristics of pacing pulses applied during subsequent executions of the at least one pacing routine to lessen a discomfort level experienced by a patient.

17. The device of claim 14, wherein the characteristics of the pacing pulses subject to adjustment include a pulse energy level, a pulse rate, and a pulse width.

18. The device of claim 14, wherein the at least one processor is further configured to process the ECG information to detect ventricular depolarization.

19. The device of claim 14, wherein determining whether the at least one pacing routine resulted in capture comprises causing the at least one processor to:
blank out ECG information signals being received via the ECG sensing electrode during a blanking interval in which at the least one pacing pulse is applied; and
detect cardiac activity immediately following the blanking interval.

20. The device of claim 19, wherein causing the at least one processor to detect cardiac activity comprises causing the at least one processor to detect intrinsic cardiac activity.

21. The device of claim 14, wherein determining whether the at least one pacing routine resulted in capture comprises causing the at least one processor to:
blank out ECG information signals being received via the ECG sensing electrode during a blanking interval in which at the least one pacing pulse is applied;
ignore ECG information signals being received via the ECG sensing electrode during a refractory interval following the blanking interval; and
detect cardiac activity immediately following the refractory interval.

22. The device of claim 21, wherein the blanking interval and the refractory interval are of substantially the same length.

23. The device of claim 21, wherein the at least one pacing pulse is a constant current pulse having a duration of 40 milliseconds, and wherein the blanking interval and the refractory interval have a combined duration of 45 milliseconds.

24. The device of claim 14, wherein the at least one processor is further configured to deliver another pacing pulse having an energy level higher than the at least one pacing pulse in response to determining that the at least one pacing pulse did not result in capture.

25. The device of claim 14, wherein the at least one processor is further configured to deliver another pacing pulse having an energy level lower than the at least one pacing pulse in response to determining that the at least one pacing pulse resulted in capture.

26. The device of claim 14, wherein the identified cardiac condition includes bradycardia and the at least one processor is configured to:
determine that a first interval has passed without detection of a heart beat; and
apply, responsive to determining that the first interval has passed, a pacing pulse via the at least one therapy electrode.

27. The device of claim 14, wherein the identified cardiac condition includes tachycardia and the at least one pacing routine comprises an anti-tachyarrhythmic pacing routine.

28. The device of claim 14, wherein the identified cardiac condition includes at least one of asystole and pulseless electrical activity and the at least one processor is configured to:
determine that a first interval has passed without detection of a heart beat; and
apply, responsive to determining that the first interval has passed, a pacing pulse via the at least one therapy electrode.

* * * * *